United States Patent
Nakaoka et al.

(10) Patent No.: US 9,308,136 B2
(45) Date of Patent: Apr. 12, 2016

(54) DISPOSABLE DIAPER

(75) Inventors: Kenji Nakaoka, Osaka (JP); Yuki Takahashi, Mima-gun (JP); Emi Amano, Mima-gun (JP)

(73) Assignee: LIVEDO CORPORATION, Ehime (JP)

( * ) Notice: Subject to any disclaimer, the term of this patent is extended or adjusted under 35 U.S.C. 154(b) by 402 days.

(21) Appl. No.: 13/807,090

(22) PCT Filed: Jun. 15, 2011

(86) PCT No.: PCT/JP2011/003415
§ 371 (c)(1),
(2), (4) Date: Dec. 27, 2012

(87) PCT Pub. No.: WO2012/001895
PCT Pub. Date: Jan. 5, 2012

(65) Prior Publication Data
US 2013/0102988 A1 Apr. 25, 2013

(30) Foreign Application Priority Data
Jun. 30, 2010 (JP) ................. P2010-149836

(51) Int. Cl.
*A61F 13/15* (2006.01)
*A61F 13/20* (2006.01)
*A61F 13/49* (2006.01)
*A61F 13/496* (2006.01)

(52) U.S. Cl.
CPC ......... *A61F 13/49001* (2013.01); *A61F 13/496* (2013.01)

(58) Field of Classification Search
CPC ................. A61F 13/49001; A61F 13/496
USPC ..................... 604/385.01, 385.201
See application file for complete search history.

(56) References Cited

U.S. PATENT DOCUMENTS

| 5,601,545 | A | 2/1997 | Glaug et al. |
| 6,368,312 | B1 | 4/2002 | Otsubo |
| 6,468,257 | B1 * | 10/2002 | Ono et al. ............ 604/391 |

(Continued)

FOREIGN PATENT DOCUMENTS

| CN | 1252983 | 5/2000 |
| CN | 1320402 | 11/2001 |

(Continued)

OTHER PUBLICATIONS

International Search Report issued Sep. 19, 2011 in International (PCT) Application No. PCT/JP2011/003415.

(Continued)

*Primary Examiner* — Tan-Uyen (Jackie) T Ho
*Assistant Examiner* — Aundria Hairell
(74) *Attorney, Agent, or Firm* — Wenderoth, Lind & Ponack, L.L.P.

(57) ABSTRACT

An outer covering sheet (4) of a pants-type disposable diaper (1) has a front part and a back part (403) to be positioned on a front side and a back side of a wearer, and a middle part lying between the front and back parts. An absorbent body (20) is attached on the outer covering sheet (4) to absorb excrement from the wearer. Both end portions of the absorbent body, positioned in the front part and the back part (403), are folded toward the inner surface (40) of the outer covering sheet (4) and bonded on the inner surface (40). It is therefore possible to prevent skin of the wearer from being irritated by edges (241) of the end portions of the absorbent body (20) when the disposable diaper (1) is worn.

16 Claims, 6 Drawing Sheets

(56) References Cited

U.S. PATENT DOCUMENTS

| | | |
|---|---|---|
| 2001/0016720 A1 | 8/2001 | Otsubo |
| 2001/0023344 A1 | 9/2001 | Oba |
| 2003/0009143 A1 | 1/2003 | Ludwig et al. |
| 2005/0137550 A1 | 6/2005 | Schmoker et al. |
| 2005/0143711 A1* | 6/2005 | Otsubo et al. ............... 604/396 |
| 2007/0043331 A1 | 2/2007 | Haruki et al. |

FOREIGN PATENT DOCUMENTS

| | | |
|---|---|---|
| CN | 1826092 | 8/2006 |
| EP | 0 933 073 | 8/1999 |
| JP | 7-18714 | 4/1995 |
| JP | 8-66426 | 3/1996 |
| JP | 2001-252304 | 9/2001 |
| JP | 2007-097979 | 4/2007 |
| JP | 2009-178383 | 9/2009 |

OTHER PUBLICATIONS

Patent Cooperation Treaty (PCT) Written Opinion of the International Searching Authority issued Sep. 19, 2011 in International (PCT) Application No. PCT/JP2011/003415.

* cited by examiner

DISPOSABLE DIAPER

BACKGROUND OF THE INVENTION

1. Technical Field

The present invention relates to a pants-type disposable diaper.

2. Description of the Related Art

A pants-type disposable diaper which has a waist opening at an upper end and a pair of leg openings on a lower part is conventionally used as one type of absorbent product for receiving excrement from a wearer. Such a disposable diaper has an outer covering sheet where a front part and a back part, to be positioned on a front side and a back side of a wearer, are continuous with each other via a middle part, and left and right ends of the front part are bonded to left and right ends of the back part, respectively, to form a waist opening and a pair of leg openings. In addition, an absorbent body to absorb excrement from the wearer is attached on the outer covering sheet so as to lie from the front part to the back part. In Japanese Patent Application Laid-Open No. 2007-97979, a pair of end holding sheets which is bonded to a front part and a back part, respectively to cover both end portions of an absorbent body in a longitudinal direction is disclosed, and the end holding sheets prevent skin of a wearer from being irritated by edges of the end portions of the absorbent body.

A disposable absorbent product disclosed in Japanese Patent Application Laid-Open No. 8-66426 has a bulky portion since an absorbent panel is formed by folding an absorbent layer (absorbent core) upon itself. In the absorbent product of JP 8-66426, the absorbent layer and the absorbent panel don't contact with skin of a wearer directly, because they are covered with a top sheet.

In a disposable diaper having end holding sheets, when compared to a disposable diaper where end holding sheets are omitted, texture in the waist region becomes hard, air permeability decreases and manufacturing cost increases. On the other hand, in a disposable diaper where end holding sheets are omitted, there may be a case where an edge of an end portion of an absorbent body irritates skin of a wearer when the end portion is curled up and the like. Thus, a disposable diaper, where end holding sheets are omitted and skin of a wearer can be prevented from being irritated by an edge of an end portion of an absorbent body, is required.

SUMMARY OF THE INVENTION

The present invention is intended for a pants-type disposable diaper which has a waist opening at an upper end and a pair of leg openings on a lower part. It is an object of the present invention to prevent skin of a wearer from being irritated by an edge of an end portion of an absorbent body.

The disposable diaper according to the present invention comprises: an outer covering sheet which is folded in a middle part lying between a front part and a back part, the front part and the back part being to be positioned on a front side and a back side of a wearer, left and right ends of the front part being bonded to left and right ends of the back part, respectively, to form a waist opening at upper ends of the front part and the back part and form a pair of leg openings under the front part and the back part, the pair of leg openings lying in left and right of the middle part; and a sheet-like absorbent body which is attached on an inner surface of the outer covering sheet to contact with the wearer and absorb excrement from the wearer, the absorbent body lying from the front part to the back part; wherein one end portion of the absorbent body which is positioned in the front part or the back part is folded toward the inner surface of the outer covering sheet to be bonded on the inner surface.

In the present invention, it is possible to prevent skin of the wearer from being irritated by an edge of the one end portion of the absorbent body when the disposable diaper is worn.

According to a preferred embodiment of the present invention, the absorbent body has a middle bond part which lies at a middle portion and which is bonded on the inner surface of the outer covering sheet, and a portion of the absorbent body which lies between a folding position of the one end portion and the middle bond part is not bonded to the one end portion and the outer covering sheet. Therefore, the vicinity of the folding position in the absorbent body can contact with the wearer closely.

According to another preferred embodiment of the present invention, an entire edge of the one end portion of the absorbent body is positioned between the inner surface of the outer covering sheet and the other portion of the absorbent body. It is therefore possible to surely prevent skin of the wearer from being irritated by the edge of the one end portion of the absorbent body.

According to an aspect of the present invention, the absorbent body comprises: an absorbent core; a back sheet which is positioned between the inner surface of the outer covering sheet and the absorbent core; and a top sheet which is positioned on an inner surface of the absorbent core; the back sheet and the top sheet are bonded to each other in the one end portion of the absorbent body, and a folding position of the one end portion is overlapped with an edge of the absorbent core or is positioned between the edge of the absorbent core and the waist opening.

In this case, an entire edge of the one end portion of the absorbent body is positioned between the inner surface of the outer covering sheet and the absorbent core. This makes it possible to surely prevent skin of the wearer from being irritated by the edge of the one end portion of the absorbent body. Preferably, the absorbent body further comprises a pair of side wall parts which lies on left and right side portions thereof and which is standing from the top sheet, and the pair of side wall parts is bonded on the top sheet at the folding position.

According to another aspect of the present invention, the disposable diaper further comprises an elastic member which contracts the one end portion of the absorbent body in a width direction of the absorbent body to form gathers in the one end portion. It is therefore possible to surely prevent skin of the wearer from being irritated by an edge of the one end portion of the absorbent body.

More preferably, the other end portion of the absorbent body is folded toward the inner surface of the outer covering sheet to be bonded on the inner surface. This makes it possible to prevent skin of the wearer from being irritated by edges of the both end portions of the absorbent body.

These and other objects, features, aspects and advantages of the present invention will become more apparent from the following detailed description of the present invention when taken in conjunction with the accompanying drawings.

DETAILED DESCRIPTION OF THE INVENTION

Figure 1:
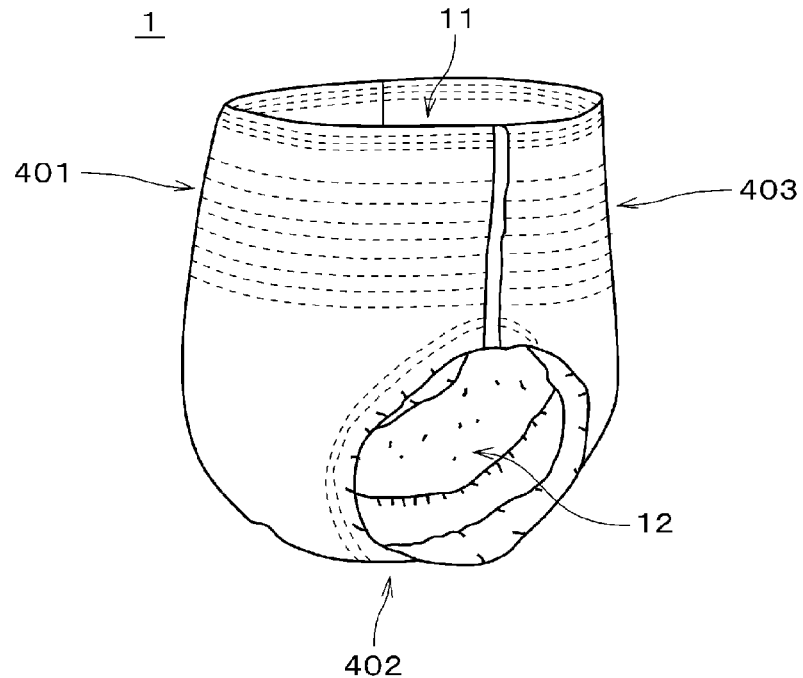
FIG. 1 is a perspective view showing an appearance of a disposable diaper in accordance with a first preferred embodiment.

FIG. 1 is a perspective view showing an appearance of a disposable diaper 1 in accordance with a first preferred embodiment of the present invention. As shown in FIG. 1, the disposable diaper 1 is a pants-type (i.e., pull-up type) diaper which has a waist opening 11 at an upper end being an end on the upper side of FIG. 1 and a pair of leg openings 12 on a lower part, and it receives excrement from a wearer. An up-down direction of FIG. 1 is not limited to the direction of gravity.

Figure 2:
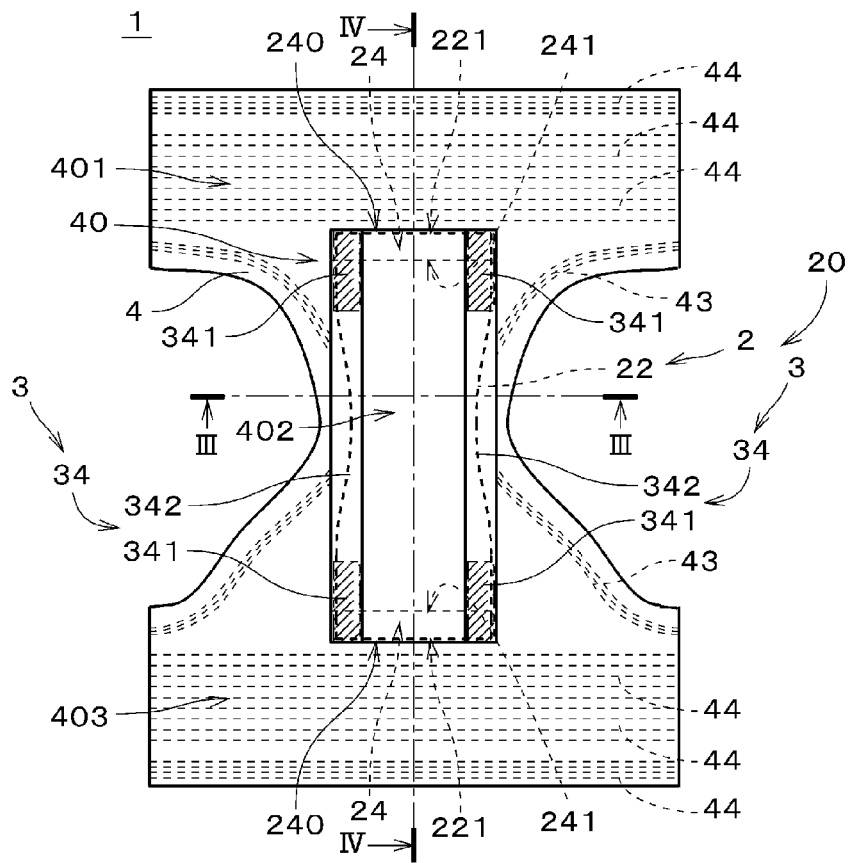
FIG. 2 is a plan view of the disposable diaper in a state where the disposable diaper is developed.

FIG. 2 is a plan view of the disposable diaper 1 in a state where the disposable diaper 1 is developed and in FIG. 2, the disposable diaper 1 is viewed from the wearer's side. As shown in FIG. 2, the disposable diaper 1 has an outer covering sheet 4 and a sheet-like absorbent body (absorber) 20 which is attached on an inner surface 40 (i.e., a surface to face the wearer) of the outer covering sheet 4 to absorb excrement from the wearer.

In the disposable diaper 1, an upper portion in FIG. 2 is to be positioned on (to cover) the front side (stomach side) of the wearer, and a lower portion in FIG. 2 is to be positioned on the back side of the wearer. In the following description, the portions of the disposable diaper 1 (and the portions of the outer covering sheet 4) to be positioned on the front side and the back side of the wearer are referred to as a "front part 401" and a "back part 403", respectively, and a portion to face a crotch region of the wearer at a position between the front part 401 and the back part 403 is referred to as a "middle part 402". The middle part 402 is continuous with both the front part 401 and the back part 403. With respect to a left-right direction (lateral direction) in FIG. 2, a width of the middle part 402 is smaller than those of the front part 401 and the back part 403. Hereinafter, the left-right direction in FIG. 2 is referred to as a "diaper width direction".

In manufacturing of the disposable diaper 1, the outer covering sheet 4 is folded at the middle part 402 together with the absorbent body 20. In the state where the middle part 402 is located on the downside, left and right ends of the front part 401 are bonded to left and right ends of the back part 403, respectively, by heat bonding (heat-sealing) under heating and pressing. As above, since the side ends of the front part 401 are bonded to the side ends of the back part 403, respectively, as shown in FIG. 1, the waist opening 11 is formed at upper ends of the front part 401 and the back part 403, and the pair of leg openings 12 lying in left and right of the middle part 402 is formed under the front part 401 and the back part 403.

Figure 3:
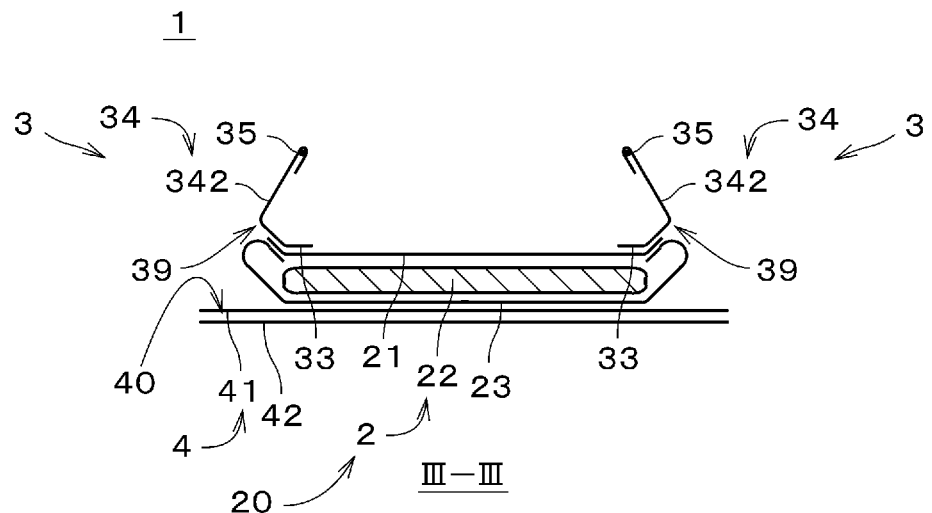
FIG. 3 is a cross-sectional view of the disposable diaper.

FIG. 3 is a cross-sectional view of the disposable diaper 1 taken along a line in FIG. 2 (cross-sectioned at the middle part 402). In FIG. 3, respective constituents of the disposable diaper 1 are drawn so as to be slightly apart from one another for the convenience of illustration.

As shown in FIG. 3, the outer covering sheet 4 has an inner sheet 41 and an outer sheet 42, and the outer sheet 42 is layered on the lower side (i.e., the side not to face the wearer) of the inner sheet 41. As shown in FIG. 2, a plurality of leg elastic members 43 and a plurality of waist elastic members 44 are bonded between the inner sheet 41 and the outer sheet 42 with hot melt adhesive or the like. In the disposable diaper 1, by contraction of the leg elastic members 43, the inner sheet 41 and the outer sheet 42 (see FIG. 3) are contracted and leg gathers are formed. Also by contraction of the waist elastic members 44, waist gathers are formed. Out of the plurality of waist elastic members 44, several waist elastic members 44 located in the vicinity of the edge of the waist opening 11 (see FIG. 1) are arranged densely, and the disposable diaper 1 fits around the wearer's waist tightly by these waist elastic members 44.

As shown in FIGS. 2 and 3, the absorbent body 20 has a sheet-like main body part 2 and a pair of side sheets 3 located on both side portions of the main body part 2 (i.e., both end portions of the main body part 2 in the diaper width direction), and the pair of side sheets 3 extends across almost the entire length of the main body part 2 in a longitudinal direction (i.e., the up-down direction in FIG. 2). As shown in FIG. 3, the main body part 2 has a top sheet 21, a back sheet 23 and an absorbent core 22 which is located between the top sheet 21 and the back sheet 23. The back sheet 23 is bonded on the outer covering sheet 4 with hot melt adhesive or the like, to fix the absorbent body 20 on the outer covering sheet 4. The contour of the absorbent core 22 is drawn by thick broken lines in FIG. 2 for easy understanding of the drawing. As shown in FIG. 2, a width of the absorbent core 22 at each end portion in the longitudinal direction is larger than that at a middle portion in the longitudinal direction. In other words, the absorbent core 22 is formed in the form of an hourglass.

As shown in FIG. 3, each side sheet 3 has a strip-like bonded part 33 and a side wall part 34. The bonded part 33 is one of two portions divided by a folding line 39 extending across almost the entire length thereof in the longitudinal direction and the bonded part 33 is positioned on the main body part 2. The side wall part 34 is the other of the two portions. The bonded part 33 is located in the vicinity of the side edge of the main body part 2, it lies across almost the entire length thereof in the longitudinal direction, and it is bonded on the upper side (i.e., the wearer's side) of the main body part 2 with hot melt adhesive.

The side wall part 34 is continuous from the bonded part 33 via the folding line 39. In the vicinities of both end portions thereof in the longitudinal direction, the side wall part 34 is laid on the bonded part 33 and fixed on the bonded part 33 by heat bonding, ultrasonic bonding or hot melt adhesive. In FIG. 2, hatching lines are drawn at each portion 341 of the side wall part 34 which is fixed on the bonded part 33 for easy understanding of the drawing. As shown in FIGS. 2 and 3, the side wall part 34 has a standing part 342 standing upward from the top sheet 21 at a middle portion thereof in the longitudinal direction. In the side wall part 34 shown in FIG. 3, an elastic member 35 is bonded on a free edge of the standing part 342, and gathers are formed in the standing part 342 by contraction of the elastic member 35.

Figure 4:
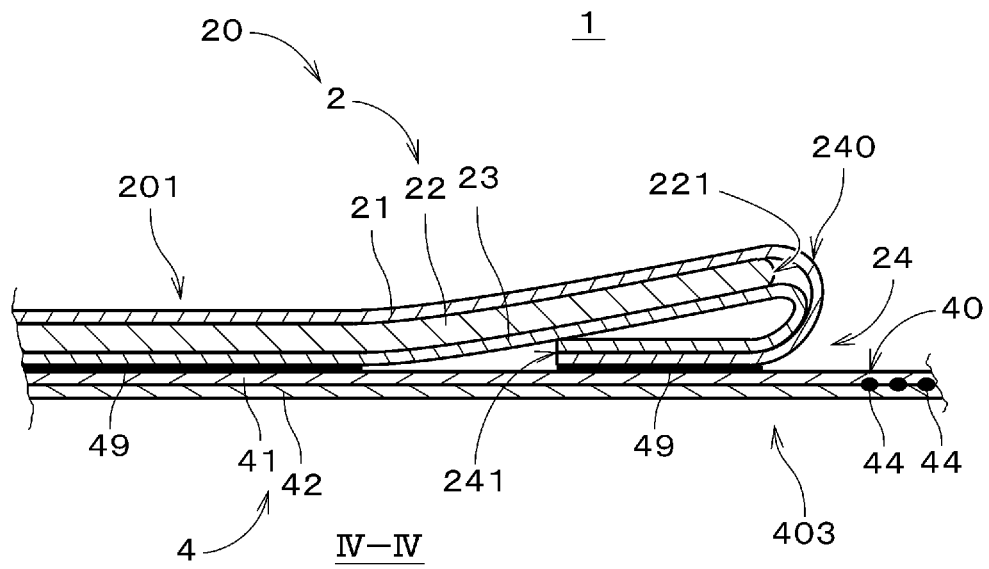
FIG. 4 is a cross-sectional view of the disposable diaper.

FIG. 4 is a cross-sectional view of the disposable diaper 1 taken (cross-sectioned) along a line IV-IV in FIG. 2. In FIG. 4, the vicinity of the end portion of the absorbent body 20 positioned in the back part 403 is shown. As shown in FIG. 2, the absorbent body 20 is located from the front part 401 to the back part 403 via the middle part 402. As shown in FIG. 4, the end portion of the absorbent body 20 positioned in the back part 403 is folded (turns back) toward the inner surface 40 of the outer covering sheet 4 to be bonded on the inner surface 40. In detail, both the back sheet 23, positioned between the inner surface 40 of the outer covering sheet 4 and the absorbent core 22, and the top sheet 21, positioned on an inner surface (i.e., a surface to face the wearer) of the absorbent core 22, are longer than the absorbent core 22 with respect to the longitudinal direction of the absorbent body 20, and portions, of the back sheet 23 and the top sheet 21, protruding in the longitudinal direction from an edge 221 (i.e., an edge almost along the diaper width direction) of the absorbent core 22, are overlapped with (laid on) and bonded to each other. In the following description, the portions of the back sheet 23 and the top sheet 21, which are bonded to each other in the end portion of the absorbent body 20 positioned in the back part 403 (the portions are denoted by a reference sign 24 in FIG. 4), are generically referred to as a "bonded end portion". A length of the bonded end portion 24 in the longitudinal direction of the absorbent body 20 is for example, 20 millimeters (mm).

The bonded end portion 24 is folded integrally (as a unit) toward the outer covering sheet 4 in the vicinity of the edge 221 of the absorbent core 22, and a surface of the bonded end portion 24 which is continuous from the inner surface of the absorbent body 20 (i.e., a surface of the top sheet 21) is bonded on the inner surface 40 of the outer covering sheet 4 with hot melt adhesive or the like. Most of the bonded end portion 24 is located between the absorbent core 22 and the inner surface 40 of the outer covering sheet 4. Also a middle portion 201 of the absorbent body 20 in the longitudinal direction is bonded on the inner surface 40 of the outer covering sheet 4, and hereinafter the portion 201 of the absorbent body 20 is referred to as a "middle bond part 201". In FIG. 4, layers of adhesive between the main body part 2 and the outer covering sheet 4 are drawn by thick solid lines denoted by reference signs 49 (the same applies to after-mentioned FIG. 7). In the disposable diaper 1 of FIG. 4, a portion of the absorbent body 20 which lies between a folding position of the bonded end portion 24 (i.e., a position denoted by a reference sign 240 in FIG. 4) and the middle bond part 201 is not bonded to the bonded end portion 24 and the outer covering sheet 4, and an end portion of the absorbent core 22 positioned in the back part 403 is slightly curved toward a direction away from the outer covering sheet 4.

Actually, since the bonded end portion 24 is folded almost along the edge 221 of the absorbent core 22, almost an entire edge 241 of a tip of the bonded end portion 24 is positioned between the inner surface 40 of the outer covering sheet 4 and the absorbent core 22 (see FIG. 2). In the disposable diaper 1 in the state where the left and right ends of the front part 401 are bonded to the left and right ends of the back part 403, respectively (see FIG. 1), a distance between the folding position 240 of the bonded end portion 24 and the waist opening 11 is smaller than a distance between the edge 221 of the absorbent core 22 and the waist opening 11 as shown in FIG. 4, and the bonded end portion 24 is folded while avoiding the absorbent core 22. In the disposable diaper 1, the folding position 240 of the bonded end portion 24 may be almost overlapped with the edge 221 of the absorbent core 22. Also in this case, the bonded end portion 24 is folded while avoiding the absorbent core 22.

As already described, each side sheet 3 (see FIGS. 2 and 3) extends over the entire lengths of the top sheet 21 and the back sheet 23 with respect to the longitudinal direction. In the bonded end portion 24, the bonded part 33 of the side sheet 3 is bonded on the top sheet 21, and the side wall part 34 is laid and fixed on the bonded part 33. As above, the pair of side wall parts 34 which is provided on the left and right side portions of the absorbent body 20 is bonded on the top sheet 21 at the folding position 240 of the bonded end portion 24, and the bonded end portion 24 can be easily folded together with the pair of side sheets 3 in manufacturing of the disposable diaper 1.

In the disposable diaper 1, the other end portion of the absorbent body 20 positioned in the front part 401 has the same structure as the end portion positioned in the back part 403 (i.e., the other end portion is also a bonded end portion 24), and it is folded toward the inner surface 40 of the outer covering sheet 4 to be bonded on the inner surface 40.

The top sheet 21 is made of liquid-pervious sheet material, and the top sheet 21 immediately catches moisture of excrement from the wearer and moves the moisture into the absorbent core 22. For example, the top sheet 21 is a liquid-pervious nonwoven fabric made of hydrophobic fibers (polypropylene, polyethylene, polyester, polyamide, nylon or the like) where hydrophilic treatment is performed on its surface with a surfactant, and examples of nonwoven fabrics used for the top sheet 21 are a point-bond nonwoven fabric, air-through nonwoven fabric, and spunbond nonwoven fabric. A nonwoven fabric (for example, spunlace nonwoven fabric) made of hydrophilic fibers such as cellulose, rayon, cotton may be used as the top sheet 21.

The absorbent core 22 is formed by wrapping a mixture of hydrophilic fibers such as crushed pulp fibers or cellulose fibers and super absorbent material such as granulated super absorbent polymers (e.g., SAP (Super Absorbent Polymer)) or super absorbent fibers in a tissue paper, a liquid-pervious nonwoven fabric or the like, and the absorbent core 22 rapidly absorbs and retains the moisture which has passed through the top sheet 21. The tissue paper, the liquid-pervious nonwoven fabric or the like to wrap the hydrophilic fibers, is bonded to the hydrophilic fibers and the absorbent material with hot melt adhesive, to prevent deformation of the hydrophilic fibers and falling of the absorbent material (especially, falling after absorption of moisture). In the present embodiment, the absorbent core 22 includes pulp fibers and SAP.

As the back sheet 23, used is a water-repellent or liquid-impervious nonwoven fabric (for example, a spunbond nonwoven fabric, meltblown nonwoven fabric or SMS (spunbond-meltblown-spunbond) nonwoven fabric) made of hydrophobic fibers, or a water-repellent or liquid-impervious plastic film. The back sheet 23 prevents moisture of excrement or the like which has come to the back sheet 23, from leaking out to the outside of the main body part 2. In a case where a plastic film is used for the back sheet 23, it is preferable that a plastic film with permeability (breathability) is used, from the view point of preventing sweatiness in the disposable diaper 1 and providing a comfortable feeling for the wearer.

As a sheet main body of the side sheet 3, used is a water-repellent or liquid-impervious nonwoven fabric (for example, a spunbond nonwoven fabric, meltblown nonwoven fabric or SMS nonwoven fabric) made of hydrophobic fibers. For example, a polyurethane yarn, strip-like polyurethane film, yarn-like or strip-like natural rubber, or the like is used as the elastic member 35. In the present embodiment, a polyurethane yarn is used as the elastic member 35.

As the inner sheet 41 and the outer sheet 42 of the outer covering sheet 4, used is a water-repellent or liquid-impervious nonwoven fabric made of hydrophobic fibers, or a water-repellent or liquid-impervious plastic film in a similar fashion to the back sheet 23. A laminated sheet of the nonwoven fabric and the plastic film may be used. It is preferable that the plastic film has permeability (breathability). In a similar fashion to the top sheet 21, a nonwoven fabric made of hydrophilic fibers or a liquid-pervious nonwoven fabric made of hydrophobic fibers where hydrophilic treatment is performed may be utilized as the inner sheet 41 and the outer sheet 42.

As the leg elastic members 43 and the waist elastic members 44, for example, a polyurethane yarn, strip-like polyurethane film, yarn-like or strip-like natural rubber, or the like is used in a similar fashion to the elastic member 35 of the side sheet 3. In the present embodiment, polyurethane yarns are utilized as the leg elastic members 43 and the waist elastic members 44.

When the disposable diaper 1 shown in FIG. 1 is put on the wearer, both legs of the wearer are inserted into the pair of leg openings 12 through the waist opening 11 and then the disposable diaper 1 is pulled up around the waist of the wearer. At this time, since the entire edges of the end portions of the absorbent body 20 shown in FIG. 2 (i.e., the edges 241 of the bonded end portions 24) are covered with the other portion of the absorbent body 20, the edges 241 don't contact with skin of the wearer. In addition, since both end portions of the absorbent core 22 positioned in the front part 401 and the back part 403 are curved toward the wearer, portions of the absorbent body 20 positioned in the vicinity of the edges 221 of the absorbent core 22 will closely contact the wearer.

As described above, in the absorbent body 20, of the disposable diaper 1, to contact with the wearer directly and absorb excrement from the wearer, the end portions positioned in the front part 401 and the back part 403 are folded back toward the inner surface 40 of the outer covering sheet 4 to be bonded on the inner surface 40. It is therefore possible to prevent skin of the wearer from being irritated by the edges 241 of the end portions of the absorbent body 20 when the disposable diaper 1 is worn. In the disposable diaper 1 where end holding sheets are omitted, when compared to a disposable diaper having end holding sheets, the texture in the waist region becomes soft and air permeability increases so that feeling of wearing the disposable diaper 1 can be improved, and also manufacturing costs of the diaper can be reduced.

In the disposable diaper 1, the entire edge 241 of each end portion of the absorbent body 20 is positioned between the inner surface 40 of the outer covering sheet 4 and the other portion of the absorbent body 20. It is therefore possible to surely prevent the skin of the wearer from being irritated by the edge 241.

Furthermore, a portion, of the absorbent body 20, which lies from the folding position 240 of each end portion to the middle bond part 201 (see FIG. 4) is not bonded to the end portion and the outer covering sheet 4. Therefore, the vicinity of the folding position 240 in the absorbent body 20 can closely contact the wearer. As a result, it is possible to prevent excrement from leaking out through the vicinity of the folding position 240. Leakage of excrement often occurs especially in the back side of the wearer. Thus, from this point of view, it is preferable that at least the portion which lies between the folding positions 240 of the bonded end portion 24 positioned in the back part 403 and the middle bond part 201 is not bonded to a turndown portion of the bonded end portion 24 and the outer covering sheet 4.

Figure 5:
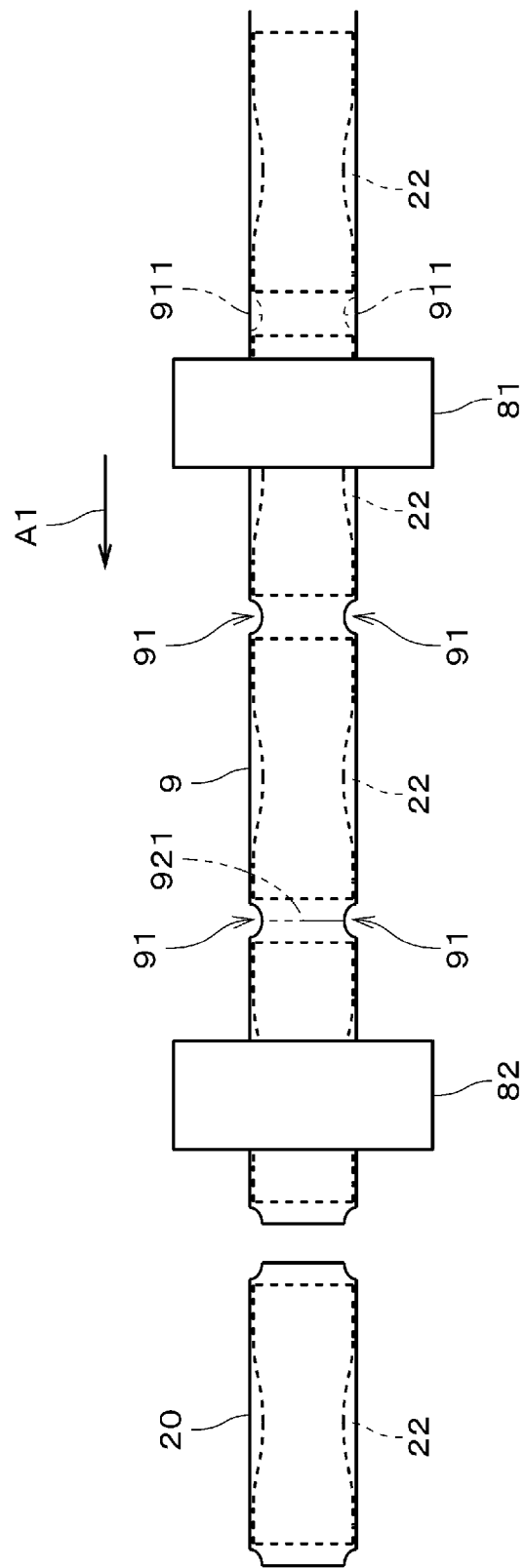
FIG. 5 is a view illustrating a part of manufacturing process of an absorbent body.

Next, discussion will be made on another example of absorbent body in the disposable diaper 1. FIG. 5 is a view explaining a part of manufacturing process of an absorbent body 20 in accordance with another example. In manufacturing process of the absorbent body 20 in accordance with another example, a continuous sheet 9, where absorbent bodies in the course of manufacturing are continuous, continuously moves in a direction shown with an arrow denoted by a reference sign A1 in FIG. 5 (i.e., the direction is a longitudinal direction of the continuous sheet 9 and hereinafter referred to as a "feed direction"). In the continuous sheet 9, a plurality of absorbent cores 22 lie between a strip-like sheet to become back sheets and a strip-like sheet to become top sheets, and the absorbent cores 22 are arranged at intervals in the feed direction A1. Actually, a pair of strip-like sheets to become side sheets is also bonded in the continuous sheet 9.

By a first cutter 81, concave parts (notched portions) 91 are formed on both side portions of each area between two adjacent absorbent cores 22 in the strip-like continuous sheet 9 passing under the first cutter 81. In FIG. 5, edges of portions to be cut down by the first cutter 81 in the continuous sheet 9 are drawn by chain double-dashed lines denoted by reference signs 911, and the almost semicircular portions are cut down in each side portion of the continuous sheet 9. Therefore, in the area between two adjacent absorbent cores 22, a width of the continuous sheet 9 (i.e., a width in a direction orthogonal to the feed direction A1) is less than that of the other portion.

By a second cutter 82, the area between two adjacent absorbent cores 22 is cut off in the continuous sheet 9 passing under the second cutter 82, and therefore a portion having only one absorbent core 22 is took out as an absorbent body 20. Specifically, as shown by a chain double-dashed line denoted by a reference sign 921 in FIG. 5, the continuous sheet 9 is cut along a line orthogonal to the feed direction A1 at a position of two concave parts 91 facing each other. Therefore, in each end portion of the absorbent body 20 which is cut off from the continuous sheet 9, a length of edge excluding the concave parts 91 (i.e., a length of the edge which is orthogonal to the feed direction A1) is less than the width of the other portion of the absorbent body 20.

When the absorbent body 20 shown in FIG. 5 is fixed on the outer covering sheet 4, the both end portions to be positioned in the front part 401 and the back part 403 are folded, at a position in the vicinities of the edges of the absorbent core 22, toward the inner surface 40 of the outer covering sheet 4 to be bonded on the inner surface 40. At this time, in the absorbent body 20 of FIG. 5 which has an approximately rectangular shape, left and right corners (both corners) of each end portion of the absorbent body 20 have chamfered shapes. Thus, even if the folding line on the absorbent body 20 is slightly tilted relative to a direction orthogonal to the longitudinal direction of the absorbent body 20 when each end portion of the absorbent body 20 is folded, the entire edge of the end portion is positioned between the inner surface 40 of the outer covering sheet 4 and the other portion of the absorbent body 20. As the result, in the disposable diaper 1, it is possible to more surely prevent skin of the wearer from being irritated by the edges of the both end portions of the absorbent body 20. In after-mentioned disposable diapers 1a, 1b, absorbent bodies whose corners have chamfered shapes may be used.

Figure 6:
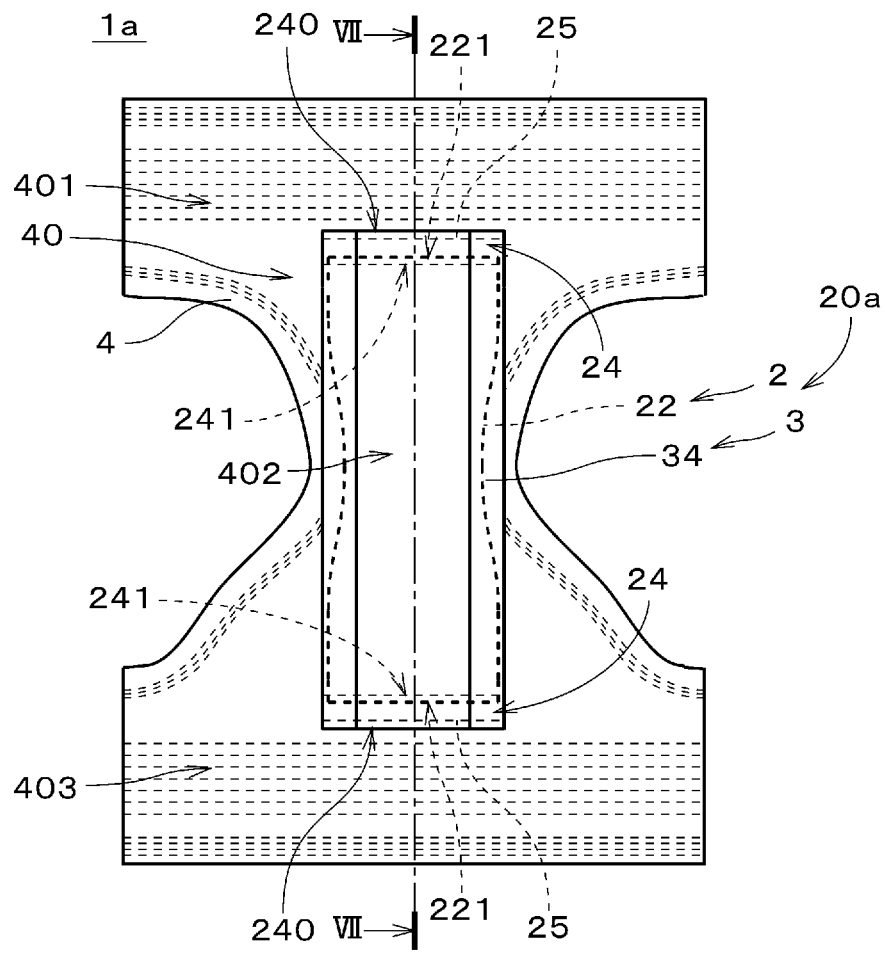
FIG. 6 is a view showing a disposable diaper in accordance with a second preferred embodiment.
Figure 7:
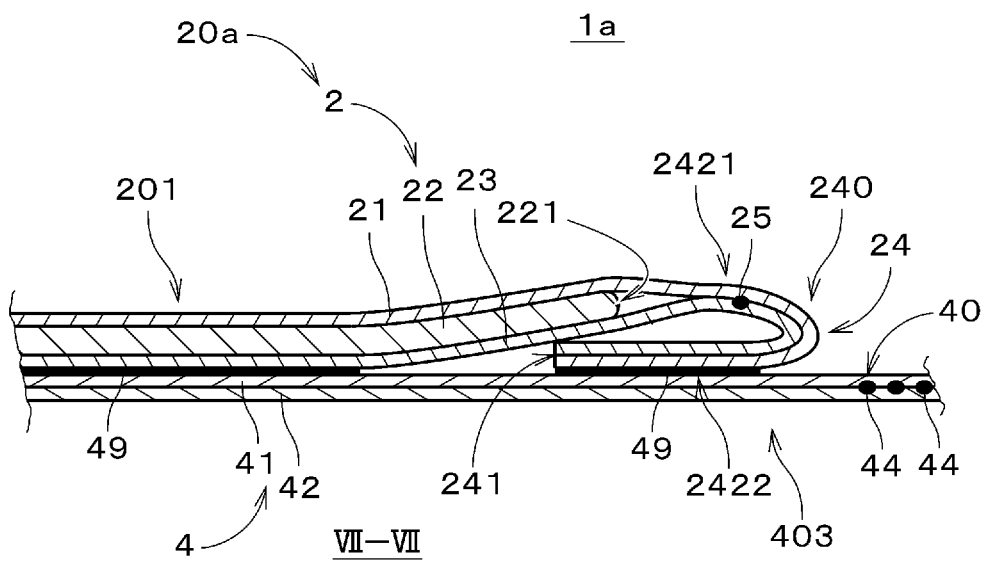
FIG. 7 is a cross-sectional view of the disposable diaper.

FIG. 6 is a view showing a disposable diaper 1a in accordance with a second preferred embodiment of the present invention, and FIG. 6 corresponds to FIG. 2. FIG. 7 is a cross-sectional view of the disposable diaper 1a taken (cross-sectioned) along a line VII-VII in FIG. 6. In FIG. 7, the vicinity of the end portion of the absorbent body 20a positioned in the back part 403 is drawn. The disposable diaper 1a in FIGS. 6 and 7 is different from the disposable diaper 1 in FIGS. 2 to 4 in the point where the absorbent body 20a has an after-mentioned elastic member 25. Constituent elements other than those are identical to those of the disposable diaper 1 in FIGS. 2 to 4 and the same elements are denoted by the same reference signs.

In the absorbent body 20a shown in FIGS. 6 and 7, the end portions positioned in the front part 401 and the back part 403 are folded toward the inner surface 40 of the outer covering sheet 4 to be bonded on the inner surface 40 in a similar fashion to the absorbent body 20 in FIG. 4. In detail, as shown in FIG. 7, portions of the back sheet 23 and the top sheet 21 lying between one edge 221 of the absorbent core 22 and the tips of them are bonded to each other as the bonded end portion 24, and the bonded end portion 24 is folded toward the inner surface 40 of the outer covering sheet 4 to be bonded on the inner surface 40. An elastic member 25 (see FIG. 6) extending in the diaper width direction is bonded between the back sheet 23 and the top sheet 21 in the bonded end portion 24, in the state where the elastic member 25 is stretched (i.e., the stretched elastic member 25 is bonded in the bonded end portion 24).

In the disposable diaper 1a, the folding position 240 of the bonded end portion 24 is slightly away from the edge 221 of the absorbent core 22, and as shown in FIG. 7, a first portion 2421 of the bonded end portion 24 which lies from the vicinity of the edge 221 of the absorbent core 22 to the folding position 240 (i.e., the portion doesn't contact with the inner surface 40 of the outer covering sheet 4) and a second portion 2422 of the bonded end portion 24 which lies from the vicinity of the folding position 240 to the edge 241 of the tip of the bonded end portion 24 (i.e., the portion contacts with the inner surface 40 of the outer covering sheet 4) become a double structure. In the present embodiment, the elastic member 25 is bonded to the above first portion 2421, however it may be bonded to the second portion 2422 (it may lie in the vicinity of the edge 241). For example, a polyurethane yarn, strip-like polyurethane film, yarn-like or strip-like natural rubber, or the like is used as the elastic member 25. In the present embodiment, a polyurethane yarn is used as the elastic member 25 (the same applies to the elastic member 45, 45a shown in FIGS. 8 and 9).

In the disposable diaper 1a in FIGS. 6 and 7, by contraction of the elastic member 25, the bonded end portion 24 (the above first portion 2421 of the bonded end portion 24) is contracted in a width direction of the absorbent body 20 (i.e., the diaper width direction) to form gathers in the bonded end portion 24. Therefore, the bonded end portion 24 becomes thick (bulky), and in the vicinity of the bonded end portion 24, a certain space is formed between the inner surface 40 of the outer covering sheet 4 and skin of the wearer when the disposable diaper 1a is worn. In other words, the gathers formed in the bonded end portion 24 function as a spacer. Thus, even if the folding line is slightly tilted relative to a direction orthogonal to the longitudinal direction of the absorbent body 20a and a part (for example, a corner) of the edge 241 of the bonded end portion 24 isn't covered with the other portion of the absorbent body 20a when the bonded end portion 24 of the absorbent body 20a is folded, the part of the edge 241 is prevented from contacting with the wearer. As above, in the disposable diaper 1a, skin of the wearer can be surely prevented from being irritated by the edge 241 of the bonded end portion 24.

Figure 8:
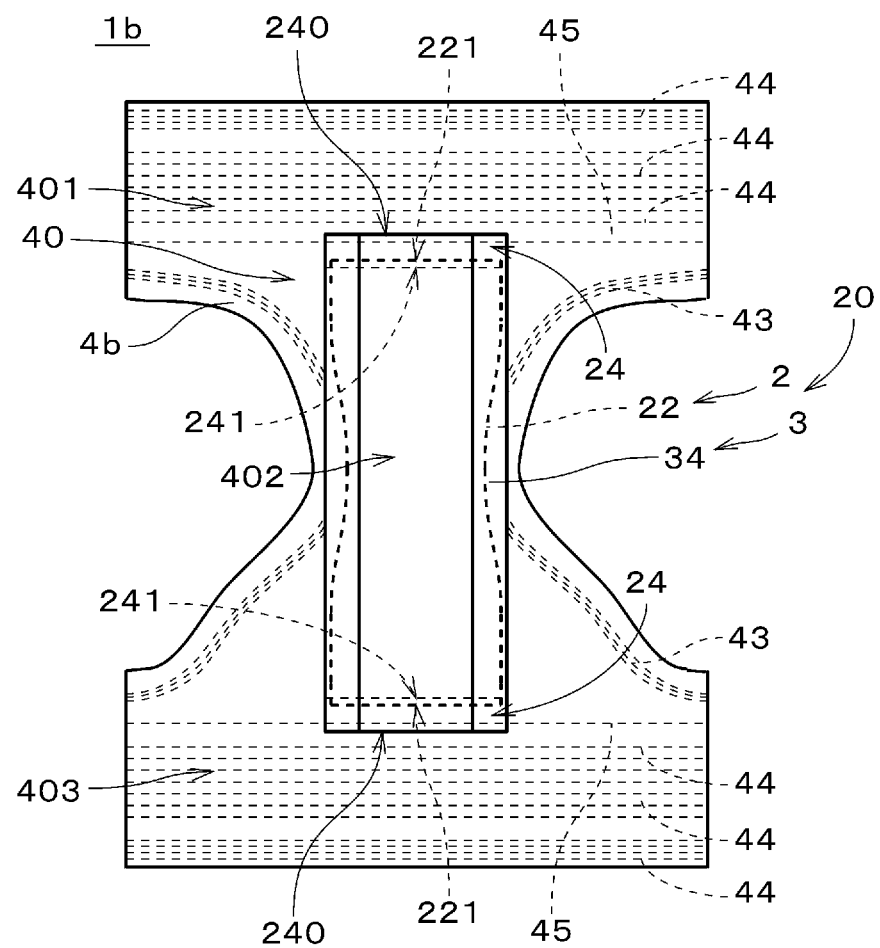
FIG. 8 is a view showing a disposable diaper in accordance with a third preferred embodiment.

FIG. 8 is a view showing a disposable diaper 1b in accordance with a third preferred embodiment of the present invention, and FIG. 8 corresponds to FIG. 2. The disposable diaper 1b in FIG. 8 is different from the disposable diaper 1 in FIG. 2 in the point where the outer covering sheet 4b has an after-mentioned elastic member 45. Constituent elements other than those are identical to those of the disposable diaper 1 in FIG. 2 and the same elements are denoted by the same reference signs.

In the disposable diaper 1b in FIG. 8, the bonded end portions 24 of the absorbent body 20 positioned in the front part 401 and the back part 403 are folded toward the inner surface 40 of the outer covering sheet 4b to be bonded on the inner surface 40 in a similar fashion to the disposable diaper 1 in FIG. 2. In each bonded end portion 24 of the absorbent body 20, the folding position 240 of the bonded end portion 24 is slightly away from the edge 221 of the absorbent core 22, and an elastic member 45 extending in the diaper width direction is bonded to the outer covering sheet 4b at a position between the edge 221 and the folding position 240 with respect to the longitudinal direction of the absorbent body 20, in the state where the elastic member 45 is stretched. Actually, the elastic member 45 is provided between the inner sheet 41 and the outer sheet 42 in a similar fashion to the leg elastic members 43 and the waist elastic members 44 (see FIG. 4).

In the disposable diaper 1b in FIG. 8, by contraction of the elastic member 45, the bonded end portion 24 of the absorbent body 20 (to be exact, a portion of the bonded end portion 24 which is bonded on the outer covering sheet 4b) is contracted to form gathers. Therefore, the bonded end portion 24 becomes thick, and in the vicinity of the bonded end portion 24, a certain space is formed between the inner surface 40 of the outer covering sheet 4b and skin of the wearer when the disposable diaper 1b is worn. Thus, even if a part of the edge 241 of the bonded end portion 24 isn't covered with the other portion of the absorbent body 20, skin of the wearer can be prevented from being irritated by the part of the edge 241.

Figure 9:
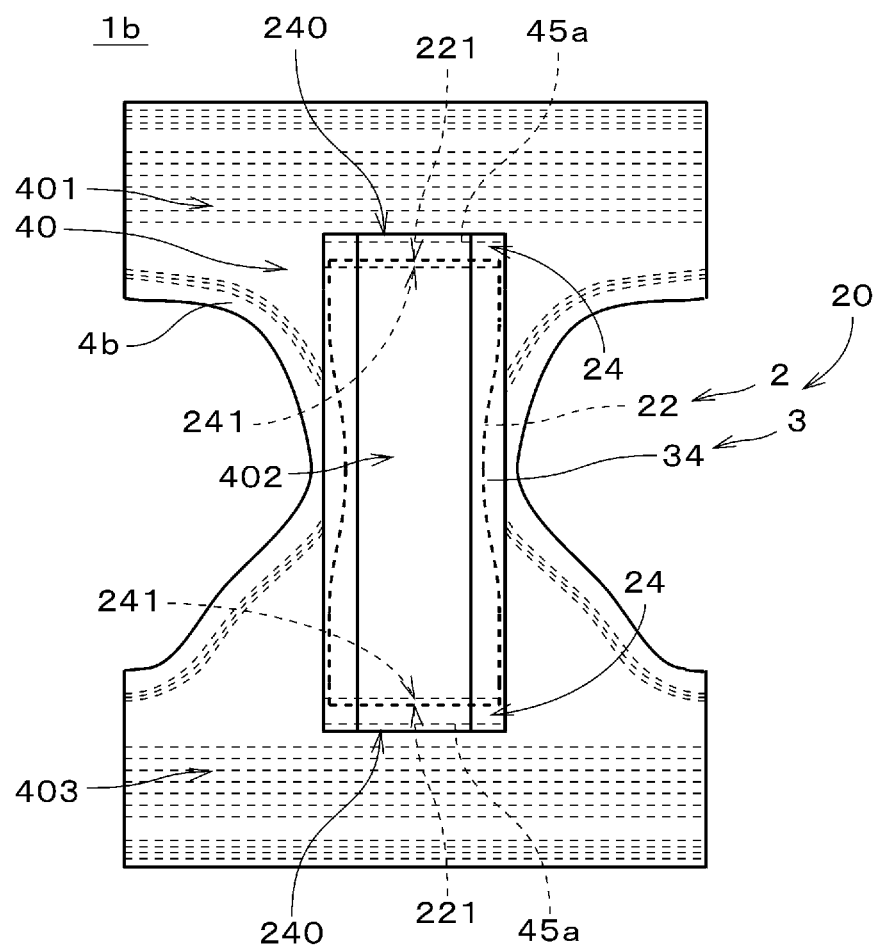
FIG. 9 is a view showing another example of disposable diaper.

FIG. 9 is a view showing another example of a disposable diaper 1b. In the disposable diaper 1b shown in FIG. 9, an elastic member 45a extending in the diaper width direction is provided on only an area, in the outer covering sheet 4b, where the absorbent body 20 exists (i.e., the are is overlapped with the absorbent body 20). As above, since the elastic member 45a is provided to only a portion which is necessary for forming gathers in the bonded end portion 24 of the absorbent body 20, a volume of polyurethane yarn used for manufacturing of the disposable diaper 1b can be reduced and manufacturing cost of the disposable diaper can be reduced. In the disposable diaper 1b in FIG. 8, since the elastic member 45 is provided across the entire width of the outer covering sheet 4b in the width direction, a polyurethane yarn to become the elastic member 45 and polyurethane yarns to become the plurality of waist elastic members 44 can be cut at the same time in manufacturing of the diaper and manufacturing of the disposable diaper 1b can be performed easily.

Though the preferred embodiments of the present invention have been discussed above, the present invention is not limited to the above-discussed preferred embodiments, but allows various variations.

In the disposable diaper 1, 1a, 1b, only one end portion of the absorbent body which is positioned in the front part 401 or the back part 403 may be folded toward the inner surface 40 of the outer covering sheet. It is therefore possible to prevent skin of the wearer from being irritated by the edge of the one end portion of the absorbent body when the disposable diaper is worn. In this case, the other end portion of the absorbent body may be covered with an end holding sheet (it is also called as an end sheet). However, from the point of view to prevent skin of the wearer from being irritated by the edges of the both end portions of the absorbent body, it is preferable that the other end portion of the absorbent body is also folded toward the inner surface 40 of the outer covering sheet to be bonded on the inner surface 40.

In the disposable diaper 1 having the absorbent body 20 shown in FIG. 5 whose corners have chamfered shapes, it is possible to surely prevent skin of the wearer from being irritated by the edge of each end portion of the absorbent body 20. However, even if a part of the edge of the end portion in the absorbent body 20 isn't covered with the other portion of the absorbent body 20 in the disposable diaper 1 of FIG. 2 having the absorbent body 20 whose corners don't have chamfered shapes, the body of the wearer is at some distance from the part of the edge by the thickness of the absorbent core 22 and therefore the part of the edge doesn't irritate skin of the wearer highly.

In the above first to third preferred embodiments, since the folding position 240 of each end portion of the absorbent body is overlapped with the edge of the absorbent core 22 or is positioned between the edge of the absorbent core 22 and the waist opening 11, the absorbent body is folded with avoiding the absorbent core 22 (i.e., the absorbent core 22 isn't folded). However, in a certain design of disposable diaper, there may be a case where the folding position of the end portion of the absorbent body is overlapped with the absorbent core 22 and a portion of the absorbent core 22 is also folded together with the top sheet 21 and the back sheet 23.

In order to avoid increase of thickness in the vicinity of the bonded end portion 24 when the disposable diaper 1, 1a, 1b is worn, the portion of the absorbent body lying between the folding position 240 of the bonded end portion 24 and the middle bond part 201 may be bonded to the turndown portion of the bonded end portion 24 and the outer covering sheet.

The constituent elements of above-discussed preferred embodiments and modified examples may be appropriately combined with one another, as long as they are not mutually exclusive.

While the invention has been shown and described in detail, the foregoing description is in all aspects illustrative and not restrictive. It is therefore understood that numerous modifications and variations can be devised without departing from the scope of the invention.

REFERENCE SIGNS LIST

1, 1a, 1b disposable diaper
4, 4b outer covering sheet
11 waist opening
12 leg opening
20, 20a absorbent body
21 top sheet
22 absorbent core
23 back sheet
24 bonded end portion
25 elastic member (in absorbent body)
34 side wall part
40 inner surface (of outer covering sheet)
45, 45a elastic member (in outer covering sheet)
201 middle bond part
221 edge (of absorbent core)
240 folding position
241 edge (of bonded end portion)
401 front part
402 middle part
403 back part

The invention claimed is:

1. A pants-type disposable diaper which has a waist opening at an upper end and a pair of leg openings on a lower part, comprising:
    an outer covering sheet which is folded in a middle part lying between a front part and a back part, said front part and said back part being adapted to be positioned on a front side and a back side of a wearer, left and right ends of said front part being bonded to left and right ends of said back part, respectively, to form a waist opening at upper ends of said front part and said back part and form a pair of leg openings under said front part and said back part, said pair of leg openings being located left and right of said middle part; and
    a sheet-like absorbent body having a top sheet, a back sheet and an absorbent core which is located between said top sheet and said back sheet,
    said absorbent body being attached on an inner surface of said outer covering sheet to contact with the wearer and absorb excrement from the wearer, said absorbent body extending from said front part to said back part,
    said back sheet being positioned between said inner surface of said outer covering sheet and said absorbent core,
    said top sheet being positioned on an inner surface of said absorbent core, wherein:
    portions of said back sheet and said top sheet protrude beyond an end of said absorbent core in a longitudinal direction of said absorbent body, and said portions of said back sheet and said top sheet are bonded to each other to form a bonded end portion;
    said bonded end portion of said absorbent body, which is positioned in said front part or said back part, is folded so as to lie between said inner surface of said outer covering sheet and said absorbent core, and said top sheet of said bonded end portion is bonded to said inner surface of said outer covering sheet; and
    an edge of said bonded end portion, formed by edges of said top sheet and said back sheet of said absorbent body, is positioned between said inner surface of said outer covering sheet and an outer surface of said back sheet of said absorbent body.

2. The disposable diaper according to claim 1, wherein said absorbent body has a middle bond part which lies at a middle portion of said absorbent body in said longitudinal direction and which is bonded to said inner surface of said outer covering sheet,
    said bonded end portion of said absorbent body is folded at a folding position, and
    a portion of said absorbent body, which lies between said folding position of said bonded end portion and said middle bond part, is not bonded to said bonded end portion or said outer covering sheet.

3. The disposable diaper according to claim 2, further comprising an elastic member which contracts said bonded end portion of said absorbent body in a width direction of said absorbent body to form gathers in said bonded end portion.

4. The disposable diaper according to claim 1, wherein an entire edge of said bonded end portion of said absorbent body is positioned between said inner surface of said outer covering sheet and said absorbent core.

5. The disposable diaper according to claim 4, further comprising an elastic member which contracts said bonded end portion of said absorbent body in a width direction of said absorbent body to form gathers in said bonded end portion.

6. The disposable diaper according to claim 1, wherein a folding position of said bonded end portion is overlapped with an edge of said absorbent core or is positioned between said edge of said absorbent core and said waist opening.

7. The disposable diaper according to claim 6, wherein an entire edge of said bonded end portion of said absorbent body is positioned between said inner surface of said outer covering sheet and said absorbent core.

8. The disposable diaper according to claim 7, further comprising an elastic member which contracts said bonded end portion of said absorbent body in a width direction of said absorbent body to form gathers in said bonded end portion.

9. The disposable diaper according to claim 6, wherein said absorbent body further comprises a pair of side wall parts which lies on left and right side portions thereof and which is standing from said top sheet, and said pair of side wall parts is bonded on said top sheet at said folding position.

10. The disposable diaper according to claim 9, further comprising an elastic member which contracts said bonded end portion of said absorbent body in a width direction of said absorbent body to form gathers in said bonded end portion.

11. The disposable diaper according to claim 6, further comprising an elastic member which contracts said bonded end portion of said absorbent body in a width direction of said absorbent body to form gathers in said bonded end portion.

12. The disposable diaper according to claim 1, wherein the other end portion of said absorbent body is folded toward said inner surface of said outer covering sheet to be bonded on said inner surface.

13. The disposable diaper according to claim 12, further comprising an elastic member which contracts said bonded end portion of said absorbent body in a width direction of said absorbent body to form gathers in said bonded end portion.

14. The disposable diaper according to claim 1, wherein said absorbent body has an approximately rectangular shape, and left and right corners of said bonded end portion of said absorbent body have chamfered shapes.

15. The disposable diaper according to claim 14, further comprising an elastic member which contracts said bonded end portion of said absorbent body in a width direction of said absorbent body to form gathers in said bonded end portion.

16. The disposable diaper according to claim 1, further comprising an elastic member which contracts said bonded end portion of said absorbent body in a width direction of said absorbent body to form gathers in said bonded end portion.

* * * * *